United States Patent [19]
Killen

[11] Patent Number: 5,961,986
[45] Date of Patent: Oct. 5, 1999

[54] ANTI-WRINKLING APPARATUS

[76] Inventor: Carolyn L. Killen, 3090 Old Hillsboro Rd., Franklin, Tenn. 37064

[21] Appl. No.: 08/608,462

[22] Filed: Feb. 28, 1996

[51] Int. Cl.[6] .................................................. A61F 13/00
[52] U.S. Cl. ............................................ 424/400; 424/449
[58] Field of Search .................................... 424/400, 449; 514/946, 947

[56] References Cited

U.S. PATENT DOCUMENTS

| | | | |
|---|---|---|---|
| 1,783,512 | 12/1930 | Mather | 2/42 |
| 2,728,079 | 12/1955 | Williams | 2/42 |
| 2,793,369 | 5/1957 | Panighini | 2/42 |
| 2,869,553 | 1/1959 | D'Or | 128/505 |
| 3,276,449 | 10/1966 | Morgan | 128/505 |
| 3,280,818 | 10/1966 | Pankey et al. | 128/505 |
| 3,297,036 | 1/1967 | Williams | 128/505 |
| 3,612,265 | 10/1971 | Dickerson | 128/156 |
| 3,934,593 | 1/1976 | Mellinger | 128/480 |
| 4,343,313 | 8/1982 | Le Jeune | 128/505 |
| 4,398,981 | 8/1983 | Ellis | 156/91 |
| 4,839,174 | 6/1989 | Baker et al. | 424/447 |
| 4,933,184 | 6/1990 | Tsuk | 424/449 |
| 4,992,074 | 2/1991 | Diaz | 450/81 |
| 5,183,459 | 2/1993 | Bernard | 602/52 |
| 5,230,896 | 7/1993 | Yeh et al. | 424/443 |
| 5,244,677 | 9/1993 | Kreckel et al. | 424/448 |
| 5,326,305 | 7/1994 | Fochler | 450/57 |
| 5,336,162 | 8/1994 | Ota et al. | 602/41 |
| 5,415,626 | 5/1995 | Goodman et al. | 602/57 |

OTHER PUBLICATIONS

Advertisement in U.S. News & World Report entitled "Your Secret Weapon Against Aging", The Magellan Group, Feb. 12, 1996.

"Handbook of Adhesives", Third Edition, Edited by Irving Skeist, Van Nostrand Reinhold, 1990.

Primary Examiner—Jose' G. Dees
Assistant Examiner—Kathryne E. Shelborne
Attorney, Agent, or Firm—Harness, Dickey & Pierce, P.L.C.

[57] ABSTRACT

The preferred embodiment of an anti-wrinkling apparatus employs a substrate with an adhesive for securing the apparatus to the user's skin for deterring skin folding and, thus, wrinkles. In another aspect of the present invention, the substrate has a substantially heart shape. In a further aspect of the present invention, the apparatus does not have a preformed shape and is flat prior to use. In yet another aspect of the present invention, the anti-wrinkling device of the present invention is applied between the breasts. In still another aspect of the present invention anti-wrinkling apparatus, multiple stacked adhesive and liner layers, as well as a substrate layer, are provided for allowing repeated application and removal.

8 Claims, 2 Drawing Sheets

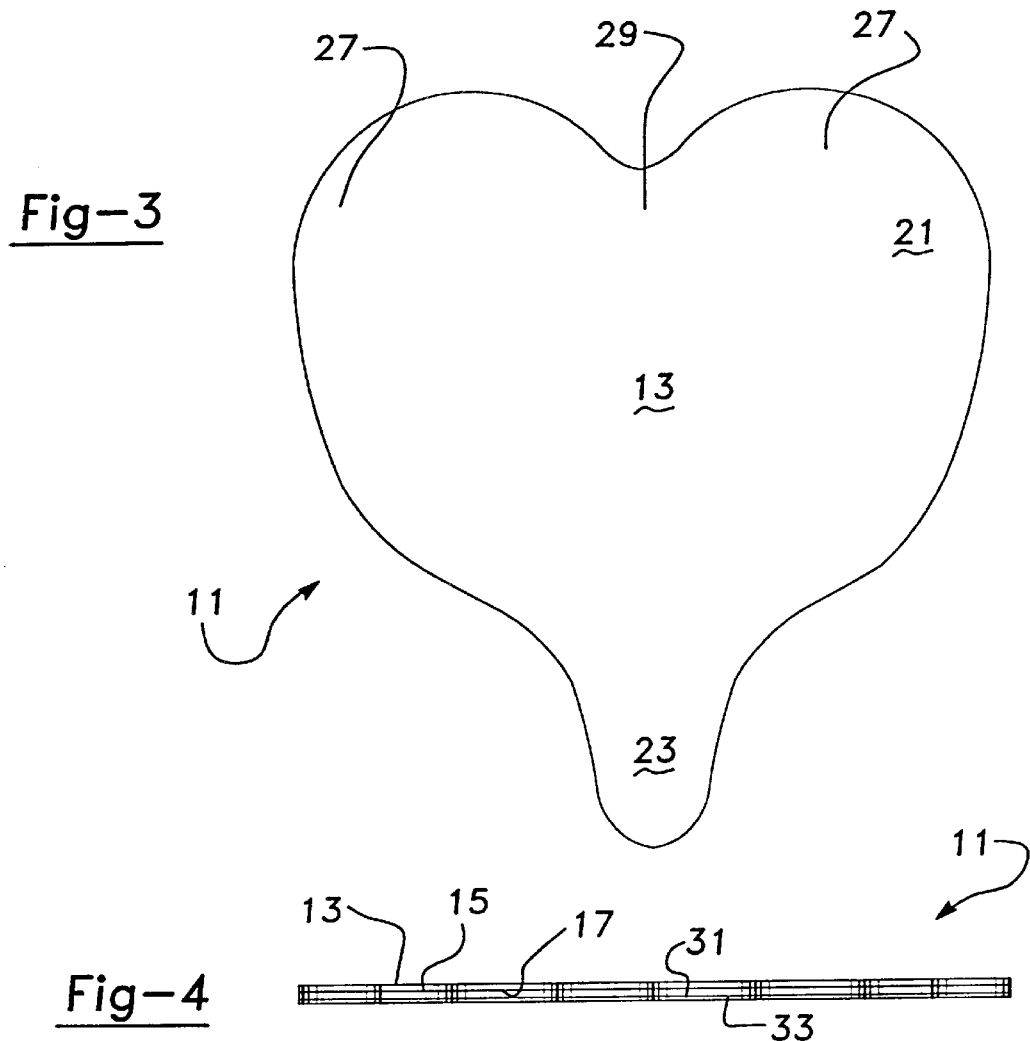
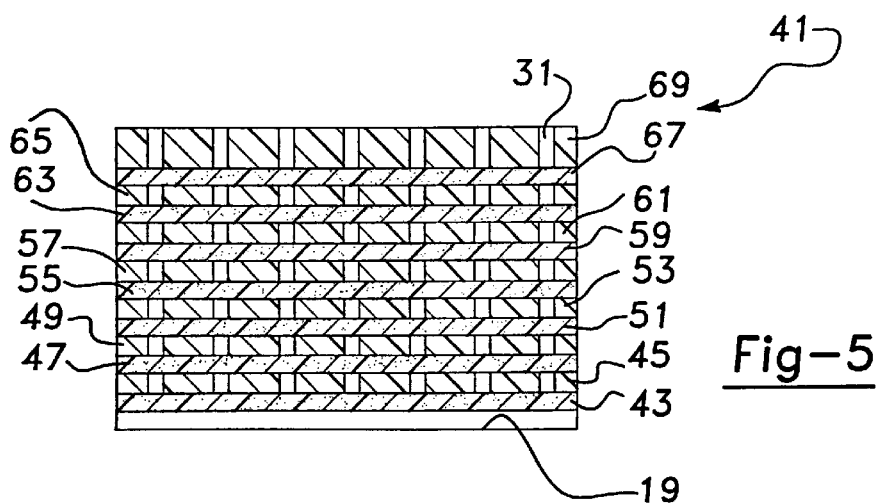

ANTI-WRINKLING APPARATUS

BACKGROUND OF THE INVENTION

This invention relates generally to devices which deter skin wrinkling and specifically to an anti-wrinkling apparatus employing an adhesive.

Wrinkles often occur in the cleavage area for many women and especially large breasted women. It is believed that this problem occurs due to the cleavage and breast skin folding upon itself or creasing when these women sleep on their sides.

Many adhesive brassiere and breast support devices are known. Examples of such prior devices are described in the following U.S. Pat. No. 4,992,074 entitled "Reusable Self-Supporting Brassiere" which issued to Diaz on Feb. 12, 1991; U.S. Pat. No. 4,343,313 entitled "Adhesive Brassiere and Its Method of Manufacture" which issued to Le Jeune on Aug. 10, 1982; U.S. Pat. No. 3,934,593 entitled "Strapless Breast Support" which issued to Mellinger on Jan. 27, 1976; U.S. Pat. No. 3,276,449 entitled "Adhesive Brassiere" which issued to Morgan on Oct. 4, 1966; U.S. Pat. No. 2,869,553 entitled "Disposable Brassiere" which issued to D'Or on Jan. 20, 1959; U.S. Pat. No. 2,728,079 entitled "Breast Support" which issued to Williams on Dec. 27, 1955; and U.S. Pat. No. 1,783,512 entitled "Protector" which issued to Mather on Dec. 2, 1930. However, none of these aforementioned patents disclose an anti-wrinkling device or any other adhesive device to be applied within the cleavage area between the breasts.

Adhesive-coated bandages are also commonplace for use in covering skin wounds. Conventional nicotine patches have also been used. Examples of such bandages and patches are disclosed within the following U.S. Pat. No. 5,415,626 entitled "Two Piece Releasable Bandage" which issued to Goodman et al. on May. 16, 1995; U.S. Pat. No. 5,336,162 entitled "Medical Bandage and Method for Using the Same" which issued to Ota et al. on Aug. 9, 1994; U.S. Pat. No. 5,244,677 entitled "Application System for Drug Containing Microemulsions" which issued to Kreckel et al. on Sep. 14, 1993; U.S. Pat. No. 5,230,896 entitled "Transdermal Nicotine Delivery System" which issued to Yeh et al. on Jul. 27, 1993; U.S. Pat. No. 5,183,459 entitled "Emulsion Pressure-Sensitive Adhesive Polymers in Bandage and Medical Tape Constructions" which issued to Bernard on Feb. 2, 1993; U.S. Pat. No. 4,839,174 entitled "Novel Transdermal Nicotine Patch" which issued to Baker et al. on Jun. 13, 1989; and U.S. Pat. No. 3,612,265 entitled "Adhesive Bandage and Envelope" which issued to Dickerson on Oct. 12, 1971; all of which are incorporated by reference herein. It should be noted that these adhesive-coated bandages and patches are typically too thin to prevent skin folding and contain an adhesive too strong for use with the more sensitive breast area. Also, the adhesive does not usually cover the entire skin-side surface of the bandage carrier. Accordingly, it would be desirable to provide an anti-wrinkling device which can effectively deter skin folding, and thus wrinkling, on a person's skin while sleeping.

SUMMARY OF THE INVENTION

In accordance with the present invention, the preferred embodiment of an anti-wrinkling apparatus employs a substrate with an adhesive for securing the apparatus to the user's skin for deterring skin folding and, thus, wrinkles. In another feature of the present invention, the substrate has a substantially heart shape. In a further feature of the present invention, the apparatus does not have a preformed shape and is flat prior to use. In yet another feature of the present invention, the anti-wrinkling device of the present invention is applied between the breasts. In still another feature of the present invention anti-wrinkling apparatus, multiple stacked adhesive and liner layers, in addition to a substrate layer, are provided for allowing repeated application and removal. Additional advantages and features of the present invention will become apparent from the following description and appended claims, taken in conjunction with the accompanying drawings.

BRIEF DESCRIPTION OF THE DRAWINGS

FIG. 3 is a true elevational view showing the preferred embodiment of the present invention anti-wrinkling apparatus; and FIG. 4 is an edge elevational view showing the preferred embodiment of the present invention anti-wrinkling apparatus.

FIG. 5 is a cross sectional view, similar to that of FIG. 2, showing an alternate embodiment of the present invention anti-wrinkling apparatus.

DETAILED DESCRIPTION OF THE PREFERRED EMBODIMENT

Figure 1:
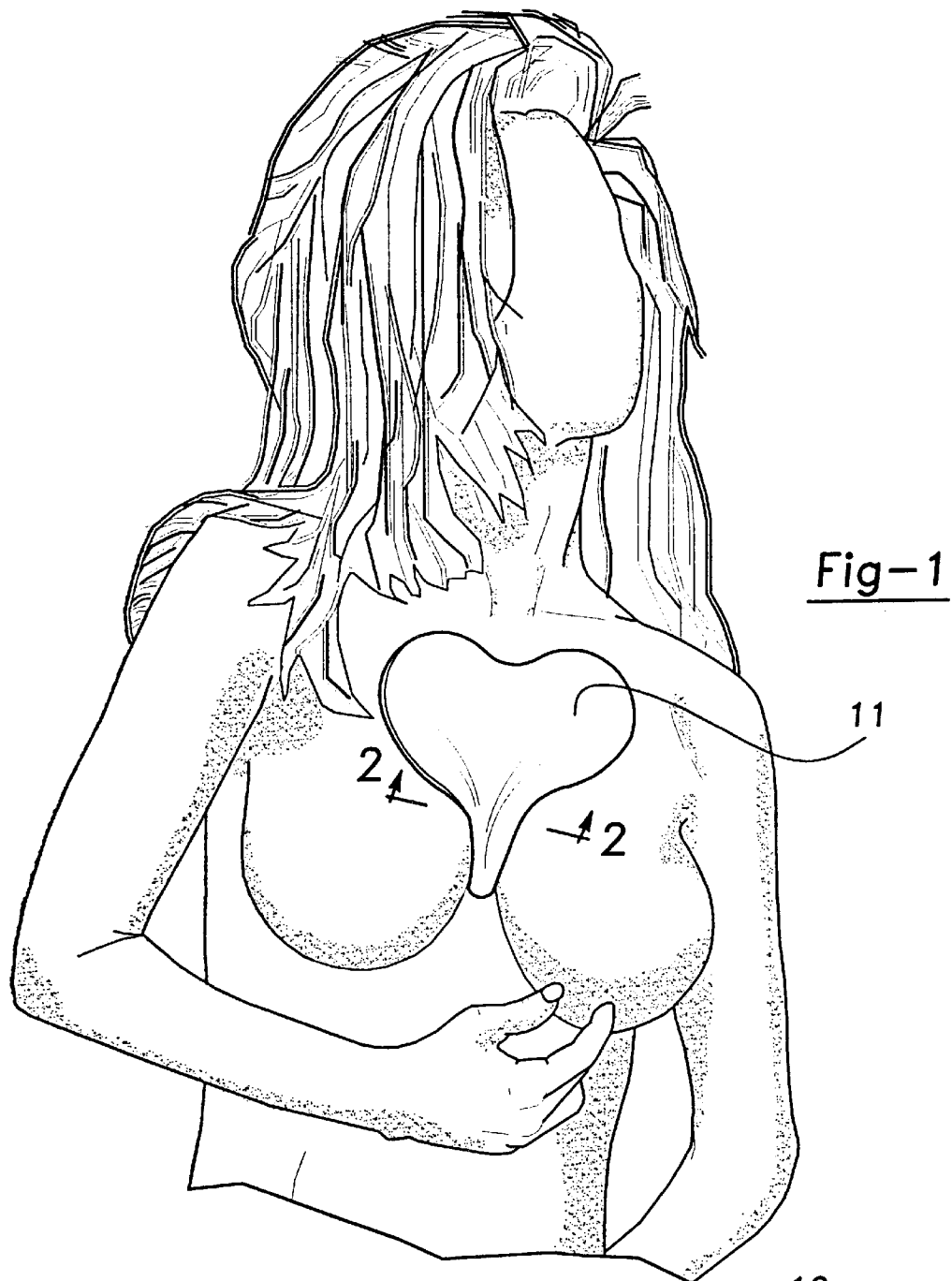
FIG. 1 is a perspective view showing the preferred embodiment of the anti-wrinkling apparatus of the present invention applied to a person's skin between and above the breasts.
Figure 2:
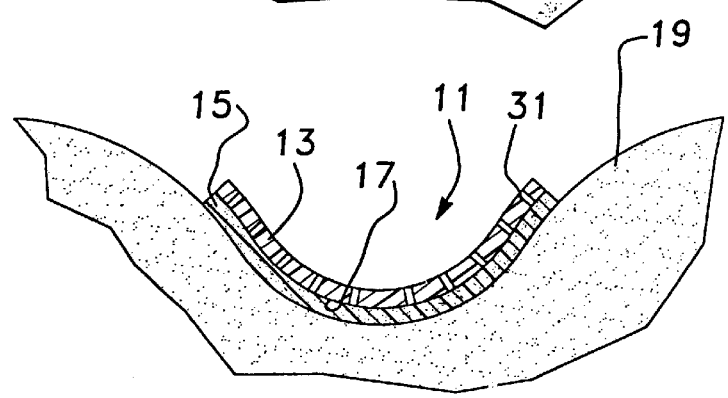
FIG. 2 is a cross sectional view, taken along line 2—2 of FIG. 1, showing the preferred embodiment of the present invention anti-wrinkling apparatus.

Referring to FIGS. 1–4, the preferred embodiment of an anti-wrinkling apparatus 11 of the present invention has a film-like substrate 13 and an adhesive layer 15. Adhesive 15 is preferably a pressure sensitive adhesive which is applied over the entire skin-side 17 of substrate 13. The adhesive coated substrate is die cut from an adhesive coated sheet of material such that anti-wrinkling apparatus 11 has an unformed, flat shape until applied to conform to a person's skin 19.

Apparatus 11 has a somewhat heart shape as shown in FIG. 3, defined by a pair of upper lobes 21 and a lower point 23. Each inner edge 27 is continuously angled in a downward and inward direction toward intersection 29.

Referring again to FIGS. 1–4, substrate 13 can be made from an open-weave or closed-weave synthetic or natural fiber material, or from a foam construction. It is desirable to have perforations 31 or the like within the substrate to encourage skin breathability so as to avoid skin irritation and sweating. The substrate has a thickness of at least 0.020 mils yet must remain somewhat flexible to allow conformance to the skin shape. In the preferred embodiment of the invention illustrated in FIGS. 1 and 3, at least 16 square inches of skin contacting surface area are provided.

The pressure sensitive adhesive should be an FDA approved material which can adhere sufficiently upon application with only light finger pressure while being suitable for easy and pain-free peeling removal. It has been found that a pressure sensitive adhesive with a peel strength less than 35 ounce inches would be suitable. Such an adhesive is preferably a rubbery type of elastomer combined with a liquid or solid tackifier component. The adhesive consequently has a high viscosity composition which would most likely be thrixeotropic in nature while maintaining some liquid characteristics. In essence, the pressure sensitive adhesive is a system composed of an elastic component, a viscous component and a visco-elastic component which work together for obtaining immediate wetting during low pressure application while having sufficient flow for retaining the wet out condition after release of the application pressure. The adhesive performance is dependent upon the following primary factors: (1) the "quick stick" ability which is the ability to wet under light pressure; (2) the adhesion ability, which is the ability to attach to another surface; and (3) the cohesive strength, which is the ability to maintain the adhesive characteristics after application. In the preferred embodiment, a releasable waxed paper liner 33 or the like is placed against the adhesive and peeled off immediately prior to application.

As is illustrated in FIG. 5, an alternate embodiment of the anti-wrinkling apparatus of the present invention is shown. In this embodiment, anti-wrinkling apparatus 41 includes a first pressure sensitive adhesive layer 43, a first liner 45, a second pressure sensitive adhesive layer 47, a second liner 49, a third pressure sensitive adhesive layer 51, a third liner 53, a fourth pressure sensitive adhesive layer 55, a fourth liner 57, a fifth pressure sensitive adhesive layer 59, a fifth liner 61, a sixth pressure sensitive adhesive layer 63, a sixth liner 65, a seventh pressure sensitive adhesive layer 67 and a single substrate 69. The liners are relatively thinner than substrate 69 and are in the range of 0.005 inch thick. Each of these layers are stacked on top of each other to form a sandwich which is flexible, yet more rigid than the preferred embodiment. The number of stacked layers can be varied as a relationship of the substrate thicknesses and tear strength. This alternate embodiment sandwich may also have a heart-like shape but is much more durable and resistant to tearing for use in repeated application to and removal from the selected skin area over a week long period. Each liner is peeled off before the next nightly use so the skin-applied adhesive will not collect contaminants such as dust or the like. However, this embodiment is still a disposable device. In contrast, the preferred embodiment is intended for single use application.

Referring again to FIGS. 1–4, it is primarily intended that the anti-wrinkling apparatus be applied to the person's skin at and above the breast cleavage as well as the immediately adjacent inside portions of the breasts, i.e. these are the areas most typically visible in casual and dressy clothing in western culture. The apparatus of the present invention is applied as follows: First, any skin oils are wiped from the skin application area. Second, the covering release liner is peeled off of the adhesive. Third, the apparatus is properly aligned between the breasts. Fourth, using the fingertips, light pressure is applied to pointed bottom 23 of the substrate to compress the apparatus against the skin. Next, pressure is gently and smoothly applied in a direction going upwardly and outwardly from pointed bottom 23 toward lobes 21 of the substrate by using both hands.

It is envisioned that the present invention will be used at night and then removed in the morning. To remove the present invention anti-wrinkling apparatus, the wearer should sponge the apparatus with water and then gently peel off the substrate from the skin. It has been found that results are improved if the skin application area is moisturized with moisturizing cream or the like immediately after removal of the apparatus.

Repeated use of the present invention anti-wrinkling apparatus significantly reduces skin wrinkling within the applied skin area. It is believed that the apparatus has sufficient rigidity and/or thickness (significantly greater than an adhesive-coated bandage or the like) such that when it is adhered to the skin, it acts to prevent skin folding and thus wrinkling. In other words, it changes the natural folding pattern of the applied skin area normally caused by the weight of the user's breasts. Thus, the present invention significantly reduces and deters skin wrinkling by increasing the bulk or folding rigidity of the skin. It is also intended that the present invention apparatus is folded in half when in its shipping and sales packaging and then unfolded when opened for use.

In a further alternate embodiment, the adhesive of the anti-wrinkling apparatus is impregnated with a medication such as a skin moisturizer or decongestant. Thus, when the apparatus is bonded to the person's chest, the medication can permeate into the skin.

While various embodiments of this anti-wrinkling apparatus have been disclosed, it will be appreciated that modifications may be made without departing from the present invention. For example, the substrate can have varying thicknesses at predetermined segments, such as where the lobes intersect. Furthermore, the present invention apparatus can be applied on the person's back between the shoulder blades and above the knee area. Various aspects of the present invention can also be applied to other body parts. Various materials have been disclosed in an exemplary fashion, however, other materials may of course be employed. It is intended by the following claims to cover these and any other departures from the disclosed embodiments which fall within the true spirit of this invention.

The invention claimed is:

1. An apparatus for deterring wrinkles of a person's skin between and above a person's breast, said apparatus comprising:

a first substrate being unformed and substantially flat prior to application on said skin;

a first pressure sensitive adhesive layer disposed along a surface of said first substrate for adhering to said skin between and above said breast, said first substrate deterring folding of said skin to which said apparatus is adhesively bonded said first pressure sensitive adhesive layer having a peel strength lass than 35 ounce inches;

a said first substrate having a skin contacting surface area of at least 16 square inches and being substantially heart-shaped, said first substrate further having a thickness of at least 20 mils such that said skin is deterred from folding within the area to which the apparatus is adhesively bonded; and a first liner disposed against said first pressure sensitive adhesive layer and being removable prior to adhesion of said first adhesive layer to the skin;

a second adhesive layer adhering to said first substrate opposite from said first adhesive layer;

a third adhesive layer;

a second liner disposed between said second and third adhesive layers, said second liner being removable prior to adhesion of said third adhesive layer to the skin; and a second substrate adhering to said third adhesive layer;

said substrate, said liners and aid adhesive layers all being disposed in a stack and parallel planer manner in relation to each other, said liners being thinner than said substrates.

2. The apparatus of claim 1 wherein said substrate has a thickness greater than 20 mils.

3. The apparatus of claim 1 wherein said substrate is strapless.

4. The apparatus of claims 1 wherein said substrate is substantially heart-shaped.

5. The apparatus of claim 1 wherein said first and second substrate have a substantially heart shaped.

6. The method of claim 1 further comprising a third substrate adhered to said second substrate in a stacked manner by a fourth adhesive layer whereby said layers are durable enough for repeated application and removal from said skin without premature tearing of said substrates.

7. The apparatus of claim 1 wherein said substrates are unformed and flat prior to application on said skin but are flexibly deformable to conform to the skin when in use.

8. The apparatus of claim 1 being applied by pressing said substrate upwardly and outwardly from a pointed bottom of said substrate toward lobes of said substrate.

\* \* \* \* \*

UNITED STATES PATENT AND TRADEMARK OFFICE
CERTIFICATE OF CORRECTION

PATENT NO. : 5,961,986
DATED : October 5, 1999
INVENTOR(S) : Carolyn L. Killen

It is certified that error appears in the above-identified patent and that said Letters Patent is hereby corrected as shown below:

Column 4, line 31, Claim 1, "of" should be -- --on;
line 40, Claim 1, after "bonded" insert -- ,--;
line 41, Claim 1, "lass" should be -- less--;
line 42, Claim 1, delete "a" (first occurrence),
line 60, Claim 1, "substrate" should be -- substrates --;
and "aid" should be -- said --;
line 61, Claim 1, "stack" should be -- stacked --;
and "planer" should be -- planar --;
Column 5, line 1, Claim 4, "claims" should be -- claim --;
line 4, Claim 5, "substrate" should be -- substrates --;
and "shaped" should be -- shape --;
line 5, Claim 6, "method" should be -- apparatus --;

Signed and Sealed this

Twenty-seventh Day of June, 2000

Attest:

Q. TODD DICKINSON

*Attesting Officer*  *Director of Patents and Trademarks*